US006551359B1

(12) United States Patent
Lang et al.

(10) Patent No.: US 6,551,359 B1
(45) Date of Patent: Apr. 22, 2003

(54) MIXTURE FOR THE OXIDATION TINTING OF KERATIN FIBRES CONTAINING A LACCASE AND TINTING METHOD USING SAID MIXTURE

(75) Inventors: Gérard Lang, Saint Prix (FR); Jean Cotteret, Verneuil/Seine (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/600,104

(22) PCT Filed: Jan. 12, 1999

(86) PCT No.: PCT/FR99/00037

§ 371 (c)(1),
(2), (4) Date: Sep. 5, 2000

(87) PCT Pub. No.: WO99/36044

PCT Pub. Date: Jul. 22, 1999

(30) Foreign Application Priority Data

Jan. 13, 1998 (FR) ............................................. 98 00252

(51) Int. Cl.⁷ .................................................. A61K 7/13
(52) U.S. Cl. ....................... 8/405; 8/401; 8/406; 8/407; 8/408; 8/410; 8/411; 8/412
(58) Field of Search ............................. 8/401, 405, 406, 8/408, 410, 411, 412

(56) References Cited

U.S. PATENT DOCUMENTS

| 3,251,742 A | | 5/1966 | Soloway ...................... 167/88 |
| 3,907,799 A | | 9/1975 | O'Brien et al. .......... 260/256.4 |
| 4,003,699 A | | 1/1977 | Rose et al. .................... 8/10.2 |
| 4,823,985 A | | 4/1989 | Grollier et al. ................. 222/1 |
| 5,061,289 A | | 10/1991 | Clausen et al. ................ 8/405 |
| 5,380,340 A | | 1/1995 | Neunhoeffer et al. .......... 8/409 |
| 5,514,188 A | | 5/1996 | Cotteret et al. ................ 8/412 |
| 5,766,576 A | | 6/1998 | Löwe et al. ................... 424/62 |
| 5,849,041 A | * | 12/1998 | Kunz et al. .................... 8/408 |
| 5,863,300 A | | 1/1999 | Audousset et al. ............ 8/411 |
| 5,948,121 A | * | 9/1999 | Aaslyng et al. ................ 8/401 |
| 5,984,975 A | * | 11/1999 | Lagrange et al. .............. 8/412 |
| 6,106,579 A | * | 8/2000 | Kunz et al. .................... 8/432 |

FOREIGN PATENT DOCUMENTS

| DE | 23 59 399 | 6/1975 |
| DE | 38 43 892 | 6/1990 |
| DE | 41 33 957 | 4/1993 |
| DE | 195 43 988 | 5/1997 |
| EP | 0 504 005 | 9/1992 |
| EP | 0 557 203 | 8/1993 |
| EP | 0 628 595 | 12/1994 |
| EP | 0 667 143 | 8/1995 |
| FR | 2 112 549 | 6/1972 |
| FR | 2 586 913 | 3/1987 |
| FR | 2 694 018 | 1/1994 |
| FR | 2 733 749 | 11/1996 |
| GB | 1 026 978 | 4/1966 |
| GB | 1 153 196 | 5/1969 |
| JP | 2-19576 | 1/1990 |
| JP | 5-163124 | 6/1993 |
| WO | WO 96/00290 | 1/1986 |
| WO | WO 94/08969 | 4/1994 |
| WO | WO 94/08970 | 4/1994 |
| WO | WO 95/07988 | 3/1995 |
| WO | WO 95/33836 | 12/1995 |
| WO | WO 95/33837 | 12/1995 |
| WO | WO 96/01644 | 1/1996 |
| WO | WO 96/15765 | 5/1996 |
| WO | WO 97/19998 | 6/1997 |
| WO | WO 97/19999 | 6/1997 |
| WO | WO 97/39727 | 10/1997 |

OTHER PUBLICATIONS

Vishnu J. Ram et al., "Synthesis of bioisosteric pyrazolo [1–5–a]pyrimidines as leishmanicides", Indian Journal of Chemistry, vol. 34B, Jun. 1995, pp. 514–520.

Robert H. Springer et al., "Synthesis and Enzymatic Activity of 6–Carbethoxy–and 6–Ethoxy–3,7–disubstituted–pyrazolo[1,5–a]pyrimidines and Related Derivatives as Adenosine Cyclic 3',5'–Phosphate Phospodiesterase Inhibitors", J. Med. Chem., vol. 25, 1982, pp. 235–242.

Thomas Novinson et al., "Synthesis and Antifungal Properties of Certain 7–Alkylaminopyrazolo[1,5–a]pyrimidines", J. Med. Chem. vol. 20, No. 2, 1977, pp. 296–299.

Nadia S. Ibrahim et al., "Studies on 3,5–Diaminopyrazoles: Synthesis of New Polyfunctionally Substituted Pyrazoloazines and Pyrazoloazoles", Archiv der Pharmazie, vol. 320, No. 3, Mar. 1987, pp. 240–246.

Alexander McKillop et al., "Reaction of Hydrazine With β–Aminocrotononitrile: Synthesis of 2,7–Dimethyl–5–Aminopyrazolo[1,5–a]pyrimidine", Heterocycles, vol. 6, Nos. 9,10, 1977, pp. 1355–1360.

Koji Saito et al., "The Reaction of Ethyl Ethoxymethylenecyanoacetate with Its Hydrazino Derivatives", Bulletin of the Chemical Society of Japan, vol. 47, No. 2, 1974, pp. 476–480.

Ermitas Alcalde, "Etude de la réaction du β–aminocrotonitrile et du α–formyl phénylacétronitrile avec l'hydrazine: synthèse d'amino–7 pyrazolo[1,5–a]pyrimidines", Journal of Heterocyclic Chemistry, vol. 11, No. 3, Jun. 1974, pp. 423–429.

\* cited by examiner

*Primary Examiner*—Necholus Ogden
*Assistant Examiner*—Eisa Elhilo
(74) *Attorney, Agent, or Firm*—Finnegan Henderson Farabow Garrett & Dunner

(57) ABSTRACT

The invention relates to a ready-to-use mixture for tinting keratin fibres, especially human keratin fibres such as hair, comprising in a support material suitable for tinting keratin fibres (a) at least one laccase-type enzyme; (b) at least one solvent selected from among certain polyols and their ethers or polyethers; and (c) at least one oxidation colorant. The invention also relates to the hair tinting method using said mixture.

32 Claims, No Drawings

MIXTURE FOR THE OXIDATION TINTING OF KERATIN FIBRES CONTAINING A LACCASE AND TINTING METHOD USING SAID MIXTURE

The present invention relates to a dyeing composition for keratinous fibres comprising at least one enzyme of the laccase type, at least one solvent chosen from certain polyols or ethers or polyethers thereof, and at least one oxidation dye, as well as its uses for dyeing keratinous fibres, in particular human hair.

It is known to dye keratinous fibres, and in particular human hair, with dyeing compositions containing oxidation dye precursors, in particular ortho- and para-phenylenediamines, ortho- or para-aminophenols, heterocyclic bases generally called oxidation bases. The oxidation dye precursors, or oxidation bases, are colourless or weakly coloured compounds which, combined with oxidizing products, can give rise to dye and coloured compounds by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of molecules used in oxidation bases and couplers allows a rich palette of colours to be obtained.

The so-called "permanent" colour obtained by means of these oxidation dyes should moreover satisfy a number of requirements. Thus, it should have no drawbacks from the toxicological point of view, it should make it possible to obtain shades of the desired intensity and it should exhibit good resistance towards external agents (light, adverse weather conditions, washing, permanent waving, perspiration, rubbing).

The dyes should also make it possible to cover grey hair, and thus should be the least selective possible, that is to say they should make it possible to obtain the smallest possible differences in colour all along the same keratinous fibre, which may indeed be differently sensitized (i.e. damaged) between its tip and its root.

The oxidation dyeing of keratinous fibres is generally carried out in an alkaline medium, in the presence of hydrogen peroxide. However, the use of alkaline media in the presence of hydrogen peroxide has the disadvantage of causing substantial degradation of the fibres, as well as decolouring of the keratinous fibres which is not always desirable.

The oxidation dyeing of keratinous fibres can also be carried out with the aid of oxidizing systems different from hydrogen peroxide such as enzymatic systems. Thus, it has already been proposed in Patent U.S. Pat. No. 3,251,742, Patent Applications FR-A-2,112,549, FR-A-2,694,018, EP-A-0,504,005, WO95/07988, WO95/33836, WO95/33837, WO96/00290, WO97/19998 and WO97/19999 to dye keratinous fibres with compositions comprising at least one oxidation dye in combination with enzymes of the laccase type, the said compositions being brought into contact with atmospheric oxygen. These dyeing formulations, although used under conditions which do not cause degradation of the keratinous fibres comparable to that caused by dyeings carried out in the presence of hydrogen peroxide, lead to colours which are still inadequate both from the point of view of homogeneity of the colour distributed along the fibre ("unison"), from the point of view of chromaticity (luminosity) and of the dyeing power.

The aim of the present invention is to solve the problems mentioned above.

The applicant has surprisingly discovered novel compositions containing, as oxidizing system, at least one enzyme of the laccase type and at least one particular solvent which will be defined in greater detail below, capable of constituting, in the presence of oxidation dye(s) (oxidation base and/or couplers), ready-to-use dyeing formulations giving colours which are more homogeneous, more intense and more chromatic without causing significant degradation or decolouring of the keratinous fibres, which exhibit low selectivity and good resistance to various attacks to which the hair may be subjected.

These discoveries form the basis of the present invention.

The first subject of the present invention is therefore a ready-to-use composition intended for dyeing human keratinous fibres, and more particularly human hair, comprising, in a carrier appropriate for dyeing keratinous fibres:

(a) at least one enzyme of the laccase type;
(b) at least one solvent chosen from
   branched or unbranched $C_3$–$C_8$ $\alpha\omega$-diols;
   branched or unbranched $C_5$–$C_8$ 1,2-1,4-1,5-2,3-2,4-2,5-2,6-2,7-2,8-3,4-3,5-3,6 diols;
   branched or unbranched $C_6$–$C_8$ 1,3 diols;
   $C_4$–$C_8$ triols;
   diethylene glycol and dipropylene glycol;
   $C_3$–$C_8$ monoalkyl ethers of $C_3$–$C_9$ glycols; $C_5$–$C_9$ monoalkyl ethers of ethylene glycol; $C_1$–$C_2$ monoalkyl ethers of $C_5$–$C_9$ glycols; $C_2$ monoalkyl ethers of 1,2-1,3-1,4-2,3-butanediols; monoalkyl ethers of glycols containing a total number of carbon atoms equal to 5;
   $C_1$–$C_9$ dialkyl ethers of $C_2$–$C_9$ glycols;
   phenyl ethers of $C_3$–$C_9$ glycols;
(c) at least one oxidation dye.

The laccase(s) used in the ready-to-use dye composition in accordance with the invention may be chosen in particular from laccases of plant origin, animal origin, fungal origin (yeasts, moulds, fungi) or bacterial origin, organisms which may be of mono- or, pluricellular origin. They can be obtained by biotechnology.

Among the laccases of plant origin which can be used according to the invention, there may be mentioned the laccases produced by plants which perform chlorophyll synthesis as indicated in Application FR-A-2,694,018 such as those found in the extracts of Anacardiaceae such as for example the extracts of *Magnifera indica, Schinus molle* or *Pleiogynium timoriense*, in the extracts of Podocarpaceae, Rosmarinus off., *Solanum tuberosum*, Iris sp., Coffea sp., *Daucus carrota, Vinca minor, Persea americana, Catharenthus roseus*, Musa sp., *Malus pumila, Gingko biloba, Monotropa hypopithys* (Indian pipe), Aesculus sp., *Acer pseudoplatanus, Prunus persica, Pistacia palaestina*.

Among the laccases of fungal origin optionally obtained by biotechnology which can be used according to the invention, there may be mentioned the laccase(s) derived from *Polyporus versicolor, Rhizoctonia practicola* and *Rhus vernicifera* as indicated in Applications FR-A-2,112,549 and EP-A-504005, those described in Patent Application WO95/07988, WO95/33836, WO95/33837, WO96/00290, WO97/19998 and WO97/19999, whose content is an integral part of the present description, such as for example those derived from Scytalidium, *Polyporus pinsitus, Myceliophtora thermophila, Rhizoctonia solani, Pyricularia orizae*, or variants thereof. There may also be mentioned those derived from *Tramates versicolor, Fomes fomentarius, Chaetomium thermophile, Neurospora crassa, Coriolus versicol, Botrytis* cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporiodes, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens and variants thereof.

The laccases of fungal origin optionally obtained by biotechnology will be preferably chosen.

The enzymatic activity of the laccases of the invention which have syringaldazine among their substrates can be defined from the oxidation of syringaldazine under aerobic conditions. The lacu unit corresponds to the quantity of enzyme catalysing the conversion of 1 mmol of syringaldazine per minute at pH 5.5 at 30° C. The unit u corresponds to the quantity of enzyme producing a delta absorbance at 530 nm of 0.001 per minute using syringaldazine as substrate, at 30° C. and at pH 6.5.

The enzymatic activity of the laccases of the invention can also be defined from the oxidation of para-phenylenediamine. The ulac unit corresponds to the quantity of enzyme producing a delta absorbance at 496.5 nm of 0.001 per minute using para-phenylenediamine as substrate (64 mM) at 30° C. and at pH 5. According to the invention, it is preferable to determine the enzymatic activity in ulac units.

The quantities of laccase used in the compositions of the invention will vary according to the nature of the laccase chosen. Preferably, they will vary from 0.5 to 2000 lacu, or from 1000 to $4 \times 10^7$ u units, or from 20 to $2 \times 10^6$ ulac units per 100 g of composition.

Polyol denotes, for the purposes of the invention, a compound of the saturated or unsaturated, linear, branched or cyclic, alkyl type carrying at least two —OH functions on the alkyl chain, as well as the polymers (polyethers) of these polyhydroxylated alkyl compounds.

For the branched or unbranched $C_3$–$C_8$ ($\alpha\omega$-diols, $\alpha\omega$ is understood, in the case of branched compounds, with respect to the longest carbon chain.

Among these compounds, there may be mentioned for example 1,3-propanediol, 1,4-butanediol, 1,5-pentanediol, 1,6-hexanediol, neopentylglycol (or 2,3-dimethyl-1,3-propanediol).

Among the branched or unbranched $C_5$–$C_8$ 1,2-1,4-1,5-2,3-2,4-2,5-2,6-2,7-2,8-3,4-3,5-3,6 diols, there may be mentioned 2,5-hexanediol, 2,4-pentanediol (or amyleneglycol), 2-methyl-2,4-pentanediol (or hexyleneglycol), 2,3-dimethyl-2,3-butanediol (or pinacol).

Among the $C_4$–$C_8$ triols, there may be mentioned in particular 1,2,4-butanetriol and 1,2,6-hexanetriol.

Among the monoalkyl ethers of glycols having a total number of carbon atoms equal to 5, there may be mentioned monoethyl ether of propylene glycol.

Among the $C_3$–$C_8$ monoalkyl ethers of $C_3$–$C_9$ glycols, there may be mentioned monobutyl ether of propylene glycol.

Among the $C_5$–$C_6$ monoalkyl ethers of ethylene glycol, there may be mentioned monohexyl ether of ethylene glycol.

Among the $C_1$–$C_2$ monoalkyl ethers of $C_5$–$C_9$ glycols, there may be mentioned monomethyl ether of dipropylene glycol, monomethyl ether of isoprene glycol, monomethyl ether of tripropylene glycol.

Among the $C_2$ monoalkyl ethers of 1,2-1,3-1,4-2,3-butanediols, there may be mentioned monomethyl ether of 2,3-butanediol.

Among the $C_1$–$C_9$ dialkyl ethers of $C_2$–$C_9$ glycols, there may be mentioned dibutyl ether of propylene glycol.

Among the phenyl ethers of $C_3$–$C_9$ glycols, there may be mentioned in particular monophenyl ether of propylene glycol and monophenyl ether of diethylene glycol.

In the present invention, it is preferable to use, as solvent:
branched or unbranched $C_3$–$C_8$ $\alpha\omega$-diols;
diethylene glycol and dipropylene glycol;
$C_3$–$C_8$ monoalkyl ethers of $C_3$–$C_9$ glycols;
$C_1$–$C_2$ monoalkyl ethers of $C_5$–$C_9$ glycols.

The polyols or their ethers or polyethers described above are present in the dyeing composition in accordance with the invention in proportions generally of between 0.1 and 40% by weight, and still more particularly from 0.5 to 20% by weight relative to the total weight of the composition.

The nature of the oxidation base(s) and/or of the couplers used in the ready-to-use dyeing composition is not critical.

The oxidation bases may be chosen in particular from para-phenylenediamines, double bases, para-aminophenols, ortho-aminophenols and heterocyclic oxidation bases.

Among the para-phenylenediamines which can be used as oxidation base in the dyeing composition in accordance with the invention, there may be mentioned in particular the compounds of the following formula (I) and their addition salts with an acid:

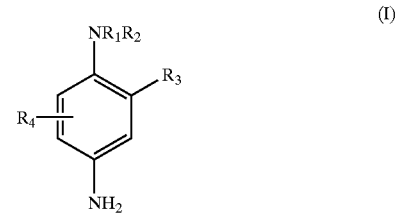

(I)

in which:
R$_1$ represents a hydrogen atom, a $C_1$–$C_4$ alkyl radical, a monohydroxy($C_1$–$C_4$ alkyl) radical, a polyhydroxy-($C_2$–$C_4$ alkyl) radical, a ($C_1$–$C_4$)alkoxy($C_1$–$C_4$)alkyl radical, a $C_1$–$C_4$ alkyl radical substituted with a nitrogen-containing group, a phenyl radical or a 4'-aminophenyl radical;

R$_2$ represents a hydrogen atom, a $C_1$–$C_4$ alkyl radical, a monohydroxy($C_1$–$C_4$ alkyl) radical, a polyhydroxy ($C_2$–$C_4$ alkyl) radical, a ($C_1$–$C_4$)alkoxy($C_1$–$C_4$)alkyl radical or a $C_1$–$C_4$ alkyl radical substituted with a nitrogen-containing group;

R$_3$ represents a hydrogen atom, a halogen atom such as a chlorine, bromine, iodine or fluorine atom, a $C_1$–$C_4$ alkyl radical, a monohydroxy($C_1$–$C_4$ alkyl) radical, a hydroxy($C_1$–$C_4$ alkoxy) radical, an acetylamino($C_1$–$C_4$ alkoxy) radical, a mesylamino($C_1$–$C_4$ alkoxy) radical or a carbamoylamino($C_1$–$C_4$ alkoxy) radical, R$_4$ represents a hydrogen or halogen atom or a $C_1$–$C_4$ alkyl radical.

Among the nitrogen-containing groups of formula (I) above, there may be mentioned in particular the amino, mono ($C_1$–$C_4$)alkylamino, ($C_1$–$C_4$)dialkylamino, ($C_1$–$C_4$) trialkylamino, monohydroxy($C_1$–$C_4$)alkylamino, imidazolinium and ammonium radicals.

Among the para-phenylenediamines of formula (I) above, there may be mentioned more particularly para-phenylenediamine, para-tolylenediamine, 2-chloro-para-phenylenediamine, 2,3-dimethyl-para-phenylene-diamine, 2,6-dimethyl-para-phenylenediamine, 2,6-diethyl-paraphenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the para-phenylenediamines of formula (I) above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

According to the invention, "double bases" is understood to mean the compounds containing at least two aromatic rings on which amino and/or hydroxyl groups are carried.

Among the double bases which can be used as oxidation bases in the dyeing compositions in accordance with the invention, there may be mentioned in particular the compounds corresponding to the following formula (II), and their addition salts with an acid:

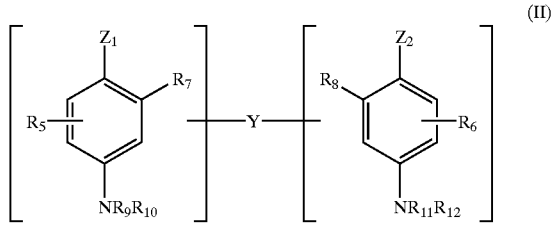

in which:
Z$_1$ and Z$_2$, which are identical or different, represent a hydroxyl or —NH$_2$ radical which may be substituted with a C$_1$–C$_4$ alkyl radical or with a linking arm Y;
the linking arm Y represents a linear or branched alkylene chain comprising from 1 to 14 carbon atoms, which may be interrupted by or which may end with one or more nitrogen-containing groups and/or one or more heteroatoms such as oxygen, sulphur or nitrogen atoms, and optionally substituted with one or more hydroxyl or C$_1$–C$_6$ alkoxy radicals;
R$_5$ and R$_6$ represent a hydrogen or halogen atom, a C$_1$–C$_4$ alkyl radical, a monohydroxy(C$_1$–C$_4$ alkyl) radical, a polyhydroxy(C$_2$–C$_4$ alkyl) radical, an amino(C$_1$–C$_4$ alkyl) radical or a linking arm Y;
R$_7$, R$_8$, R$_9$, R$_{10}$, R$_{11}$, and R$_{12}$, which are identical or different, represent a hydrogen atom, a linking arm Y or a C$_1$–C$_4$ alkyl radical;
it being understood that the compounds of formula (II) contain only one linking arm Y per molecule.

Among the nitrogen-containing groups of formula (II) above, there may be mentioned in particular the amino, mono (C$_1$–C$_4$) alkylamino, (C$_1$–C$_4$) dialkylamino, (C$_1$–C$_4$) trialkylamino, monohydroxy(C$_1$–C$_4$)alkylamino, imidazolinium and ammonium radicals.

Among the double bases of formulae (II) above, there may be mentioned more particularly N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis (2,5-diaminophenoxy)-3,5-dioxaoctane, and their addition salts with an acid.

Among these double bases of formula (II), N,N'-bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid are particularly preferred.

Among the para-aminophenols which can be used as oxidation bases in the dyeing compositions in accordance with the invention, there may be mentioned in particular the compounds corresponding to the following formula (III), and their addition salts with an acid:

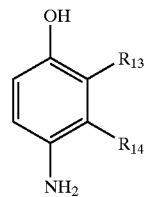

in which:
R$_{13}$ represents a hydrogen or halogen atom, a C$_1$–C$_4$ alkyl, monohydroxy(C$_1$–C$_4$ alkyl), (C$_1$–C$_4$)alkoxy (C$_1$–C$_4$)alkyl, amino(C$_1$–C$_4$ alkyl) or hydroxy(C$_1$–C$_4$) alkylamino(C$_1$–C$_4$ alkyl) radical,
R$_{14}$ represents a hydrogen or halogen atom, a C$_1$–C$_4$ alkyl, monohydroxy(C$_1$–C$_4$ alkyl), polyhydroxy (C$_2$–C$_4$ alkyl), amino(C$_1$–C$_4$ alkyl), cyano(C$_1$–C$_4$ alkyl) or (C$_1$–C$_4$) alkoxy (C$_1$–C$_4$) alkyl radical, it being understood that at least one of the radicals R$_{13}$ or R$_{14}$ represents a hydrogen atom.

Among the para-aminophenols of formula (III) above, there may be mentioned more particularly para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols which can be used as oxidation bases in the dyeing compositions in accordance with the invention, there may be mentioned more particularly 2-aminophenol, 2-amino-5-methylphenol, 2-amino-6-methylphenol, 5-acetamido-2-aminophenol, and their addition salts with an acid.

Among the heterocyclic bases which can be used as oxidation bases in the dyeing compositions in accordance with the invention, there may be mentioned more particularly pyridine derivatives, pyrimidine derivatives, pyrazole derivatives, pyrazolopyrimidine derivatives, and their addition salts with an acid.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or Japanese Patents JP 88-169,571 and JP 91-333,495 or Patent Application WO 96/15765, such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their addition salts with an acid.

Among the pyrazole derivatives, there may be mentioned more particularly the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-Methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts with an acid.

Among the pyrazolopyrimidine derivatives, there may be mentioned more particularly the pyrazolo[1,5-a]pyrimidines of the following formula (IV), their addition salts with an acid or with a base and their tautomeric forms, when a tautomeric equilibrium exists:

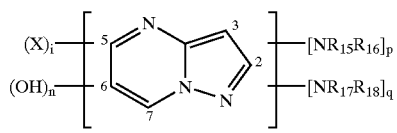

(IV)

in which:

$R_{15}$, $R_{16}$, $R_{17}$ and $R_{18}$, which are identical or different, denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a $(C_1$–$C_4)$alkoxy($C_1$–$C_4$ alkyl) radical, a $C_1$–$C_4$ aminoalkyl radical (it being possible for the amine to be protected with an acetyl, ureido or sulphonyl radical), a $(C_1$–$C_4)$ alkylamino ($C_1$–$C_4$ alkyl) radical, a di-[($C_1$–$C_4$)alkyl]amino($C_1$–$C_4$ alkyl) radical (it being possible for the dialkyl radicals to form a carbon-containing ring or a 5- or 6-membered heterocycle), a hydroxy($C_1$–$C_4$)alkyl- or di-[hydroxy ($C_1$–$C_4$)alkyl]-amino($C_1$–$C_4$ alkyl) radical, the X radicals, which are identical or different, denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a $C_1$–$C_4$ aminoalkyl radical, a $(C_1$–$C_4)$ alkylamino($C_1$–$C_4$ alkyl) radical, a di-[($C_1$–$C_4$)alkyl]amino($C_1$–$C_4$ alkyl) radical (it being possible for the dialkyls to form a carbon-containing ring or a 5- or 6-membered heterocycle), a hydroxy($C_1$–$C_4$)alkyl or di-[hydroxy($C_1$–$C_4$)alkyl]-amino($C_1$–$C_4$ alkyl) radical, an amino radical, a $(C_1$–$C_4)$alkyl- or di-[($C_1$–$C_4$)alkyl]-amino radical; a halogen atom, a carboxylic acid group, a sulphonic acid group;

i equals 0, 1, 2 or 3;

p equals 0 or 1;

q equals 0 or 1;

n equals 0 or 1;

with the proviso that:

the sum p+q is different from 0;

when p+q is equal to 2, then n equals 0 and the groups $NR_{15}R_{16}$ and $NR_{17}R_{18}$ occupy positions (2,3); (5,6); (6,7); (3,5) or (3,7);

when p+q is equal to 1, then n equals 1 and the group $NR_{15}R_{16}$ (or $NR_{17}R_{18}$) and the OH group occupy positions (2,3); (5,6); (6,7); (3,5) or (3,7).

When the pyrazolo[1,5-a]pyrimidines of formula (IV) above are such that they comprise a hydroxyl group on one of the positions 2, 5 or 7 at the α position with respect to a nitrogen atom, a tautomeric equilibrium exists which is represented for example by the following scheme:

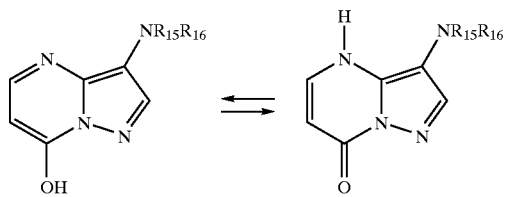

Among the pyrazolo[1,5-a]pyrimidines of formula (IV) above, there may be mentioned in particular:

pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)(2-hydroxyethyl)amino]ethanol;
2-[(7-aminopyrazolo[1,5-a]pyrimidin-3-yl)(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;

and their addition salts and their tautomeric forms, when a tautomeric equilibrium exists.

The pyrazolo[1,5-a]pyrimidines of formula (IV) above may be prepared by cyclization from an aminopyrazole according to the syntheses described in the following references:

EP 628559 BEIERSDORF-LILLY
R. Vishdu, H. Navedul, Indian J. Chem., 34b(6), 514, 1995.
N. S. Ibrahim, K. U. Sadek, F. A. Abdel-Al, Arch. Pharm., 320, 240, 1987.

R. H. Springer, M. B. Scholten, D. E. O'Brien, T. Novinson, J. P. Miller, R. K. Robins, J. Med. Chem., 25, 235, 1982.

T. Novinson, R. K. Robins, T. R. Matthews, J. Med. Chem., 20, 296, 1977.

U.S. Pat. No. 3,907,799 ICN PHARMACEUTICALS

The pyrazolo[1,5-a]pyrimidines of formula (IV) above can also be prepared by cyclization from hydrazine according to the syntheses described in the following references:

A. McKillop and R. J. Kobilecki, Heterocycles, 6(9), 1355, 1977.

E. Alcade, J. De Mendoza, J. M. Marcia-Marquina, C. Almera, J. Elguero, J. Heterocyclic Chem., 11(3), 423, 1974.

K. Saito, I. Hori, M. Higarashi, H. Midorikawa, Bull. Chem. Soc. Japan, 47(2), 476, 1974.

The oxidation base(s) in accordance with the invention preferably represent from 0.0005 to 12% by weight approximately of the total weight of the ready-to-use dyeing composition, and still more preferably from 0.005 to 6% by weight approximately of this weight.

The coupler(s) which can be used in the ready-to-use dyeing composition in accordance with the invention are those conventionally used in oxidation dyeing compositions, that is to say meta-phenylene-diamines, meta-aminophenols and meta-diphenols, mono- or polyhydroxylated derivatives of naphthalene, sesamol and its derivatives and heterocyclic compounds such as for example indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, 3,5-pyrazolinediones, pyrrolo[3,2-d]oxazole derivatives, pyrazolo[3,4-d]thiazole derivatives, thiazoloazole S-oxide derivatives, thiazoloazole S,S-dioxide derivatives, and their addition salts with an acid.

These couplers may be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole, 6-methylpyrazolo[1,5-a]benzimidazole, and their addition salts with an acid.

These couplers preferably represent from 0.0001 to 10% by weight approximately of the total weight of the ready-to-use dyeing composition, and still more preferably from 0.005 to 5% by weight approximately of this weight.

In general, the addition salts with an acid which can be used in the context of the dyeing compositions of the invention (oxidation bases and couplers) are in particular chosen from hydrochlorides, hydrobromides, sulphates and tartrates, lactates and acetates.

The dyeing composition of the invention may also contain, in addition to the oxidation dyes defined above, direct dyes in order to increase the shimmer of the shades. These direct dyes may in particular then be chosen from the nitro, azo or anthraquinone dyes.

The subject of the invention is also a method of dyeing keratinous fibres, and in particular human keratinous fibres such as hair, using the ready-to-use dyeing composition as defined above.

According to this method, at least one ready-to-use dyeing composition as defined above is applied to the fibres for a sufficient time to develop the desired colour, after which they are rinsed, optionally washed with shampoo, rinsed again and dried.

The time necessary for the development of the colour on the keratinous fibres is generally between 3 and 60 minutes and still more precisely 5 and 40 minutes.

According to one particular embodiment of the invention, the method comprises a preliminary step consisting in storing in a separate form, on the one hand, a composition (A) comprising, in a medium appropriate for dyeing, at least one oxidation dye as defined above and, on the other hand, a composition (B) containing, in a medium appropriate for dyeing, at least one enzyme of the laccase type and at least one solvent chosen from polyols or ethers or polyethers thereof as defined above, and then in mixing them at the time of use before applying this mixture to the keratinous fibres.

According to one particular embodiment of the invention, the solvent [polyols(s) or ethers or polyethers thereof] can be incorporated into the composition (A).

Another subject of the invention is a multi-compartment device or dyeing (kit) or any other multi-compartment packaging system in which a first comparment contains the composition (A) as defined above and a second compartment contains a composition (B) as defined above. These devices may be equipped with a means which makes it possible to deliver the desired mixture to the hair, such as the devices described in Patent FR-2,586,913 in the name of the applicant.

The medium appropriate for keratinous fibres (or carrier) of the ready-to-use dyeing compositions for keratinous fibres in accordance with the invention generally consists of a mixture of water and of at least one polyol or an ether or polyether thereof, as defined above. It may additionally contain organic solvents(s) different from polyols or ethers or polyethers thereof used in accordance with the invention, in order to solubilize the compounds which might not be sufficiently soluble in the medium. As organic solvent, there may be mentioned for example $C_1$–$C_4$ alkanols such as ethanol and isopropanol as well as aromatic alcohols such as benzyl alcohol, similar products and mixtures thereof.

The said organic solvents may be present in proportions preferably of between 0.5 and 40% by weight approximately relative to the total weight of the dyeing composition, and still more preferably between 1 and 20% by weight approximately.

The pH of the ready-to-use dyeing compositions for keratinous fibres in accordance with the invention is chosen such that the enzymatic activity of the laccase is not impaired. It generally varies between 4 and 11 approximately, and more preferably between 6 and 9 approximately.

The ready-to-use dyeing compositions for kertinous fibres in accordance with the invention may also contain various adjuvants conventionally used in hair dyeing compositions, such as anionic, cationic, nonionic, amphoteric or zwitterionic surfactants or mixtures thereof, polymers, thickeners, antioxidants, enzymes different from the laccases used in accordance with the invention, such as for example peroxidases or oxidoreductases containing 2 electrons, penetrating agents, sequestering agents, perfumes, buffers, dispersing agents, film-forming agents, screening agents, vitamins, preservatives or opacifying agents.

Of course, persons skilled in the art will be careful to choose this or these optional additional compounds such that the advantageous properties intrinsically attached to the dyeing compositions in accordance with the invention are not, or substantially not, impaired by the addition(s) envisaged.

The ready-to-use dyeing compositions for keratinous fibres in accordance with the invention can be provided in various forms, such as in the form of liquids, creams, gels, optionally pressurized, or in any other form appropriate for dyeing keratinous fibres, in particular human hair.

In the dyeing compositions of the invention, the oxidation dye(s) and the laccase(s) are present in the said composition which should be free of gaseous oxygen, so as to avoid any premature oxidation of the oxidation dye(s).

Concrete examples illustrating the invention will now be given.

In the text which follows or in the preceding text, unless otherwise stated, the percentages are expressed by weight.

The following examples illustrate the invention with no limitation being implied.

DYEING EXAMPLES 1 and 2

The following ready-to-use dyeing compositions were prepared (contents in grams):

| COMPOSITION | 1 | 2 |
|---|---|---|
| Laccase obtained from Rhus vernicifera containing 180 units/mg sold by the company SIGMA. | 1.8 | 1.8 |
| para-Phenylenediamine | 0.254 | 0.254 |
| 2,4-Diaminophenoxyethanol.2HCl | 0.260 | 0.260 |
| Nonionic surfactant: alkyl polyglucoside in aqueous solution containing 60% of active substance (AS) sold under the name ORAMIX CG110 by the company SEPPIC | 4.800 (AS) | 4.800 (AS) |
| Polyol according to the invention | 20 | 20 |
| pH agent   qs   pH | 6.5 | 6.5 |
| Demineralized water   qs | 100 | 100 |

Composition (1): 1,4-butanediol.
Composition (2): monobutyl ether of propylene glycol.

The ready-to-use dyeing compositions described above were applied at a temperature of 30° C. to locks of natural grey hair which is 90% white for 40 minutes. The hair is then rinsed, washed with a standard shampoo and then dried. The hair was dyed in a bluish-grey colour in both cases.

In the examples described above, 1.8% of Rhus vernicifera laccase at 180 units/mg can be replaced by 1% of Pyricularia Orizae laccase at 100 units/mg sold by the company I.C.N.

What is claimed is:
1. A composition for dyeing of keratinous fibers, comprising:
   (a) at least one enzyme of the laccase type;
   (b) at least one solvent chosen from
      branched and unbranched $C_3$–$C_8$ αω-*diols*;
      branched and unbranched $C_5$–$C_8$ 1,2; 1,4; 1,5; 2,3; 2,4; 2,5; 2,6; 2,7; 2,8; 3,4; 3,5; -and 3,6 diols;
      branched and unbranched $C_6$–$C_8$ 1,3 diols;
      $C_4$–$C_8$ triols;
      diethylene glycol and dipropylene glycol;
      $C_3$–$C_8$ monoalkyl ethers of $C_3$–$C_9$ glycols;
      $C_5$–$C_9$ monoalkyl ethers of ethylene glycol;
      $C_1$–$C_2$ monoalkyl ethers of $C_5$–$C_9$ glycols;
      $C_2$ monoalkyl ethers of 1,2; 1,3; 1,4 and 2,3-butanediols;
      monoalkyl ethers of glycols, wherein a total number of carbon atoms is equal to 5;
      $C_1$–$C_9$ dialkyl ethers of $C_2$–$C_9$ glycols; and
      phenyl ethers of $C_3$–$C_9$ glycols; and
   (c) at least one oxidation dye.
2. A composition according to claim 1, wherein said keratinous fibers are human keratinous fibers.
3. A composition according to claim 2, wherein said human keratinous fibers are hair.
4. A composition according to claim 1, wherein said at least one enzyme of the laccase type is chosen from laccases of plant origin, animal origin, fungal origin, and bacterial origin, and laccases obtained by biotechnology.
5. A composition according to claim 1, wherein said at least one enzyme of the laccase type is chosen from those produced by plants performing chlorophyll synthesis.
6. A composition according to claim 1, wherein said at least one enzyme of the laccase type is chosen from those extracted from plants chosen from Anacardiaceae, Podocarpaceae, Rosmarinus off., *Solanum tuberosum*, Iris sp., Coffea sp., *Daucus carrota, Vinca minor, Persea americana, Catharenthus roseus*, Musa sp., *Malus pumila, Gingko biloba, Monotropa hypopithys*, Aesculus sp., *Acer pseudoplatanus, Prunus persica*, and *Pistacia palaestina*.
7. A composition according to claim 1, wherein said at least one enzyme of the laccase type is chosen from those derived from fungi chosen from *Pyricularia orizae, Polyporus versicolor, Rhizoctonia praticola, Rhus vernifera, Scytalidium, Polyporus pinsitus, Myceliophtora thermophila, Rhizoctonia solani, Tramates versicolor, Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens* and variants of all of said fungi.
8. A composition according to claim 1, wherein said at least one enzyme of the laccase type is in a quantity ranging from 0.5 to 2000 ulac units per 100 g of said composition.
9. A composition according to claim 1, wherein said at least one enzyme of the laccase type is in a quantity ranging from 20 to $2\times10^6$ ulac units per 100 g of said composition.
10. A composition according to claim 1, wherein said at least one enzyme of the laccase type is in a quantity ranging from 1000 to $4\times10^7$ u unites per 100 g of said composition.
11. A composition according to claim 1, wherein said at least one solvent is chosen from:
   branched and unbranched $C_3$–$C_8$ αω-diols;
   diethylene glycol and dipropylene glycol;
   $C_3$–$C_6$ monoalkyl ethers of $C_3$–$C_9$ glycols; and
   $C_1$–$C_2$ monoalkyl ethers of $C_5$–$C_9$ glycols.
12. A composition according to claim 1, wherein said at least one solvent is present in a concentration ranging from 0.1% to 40% by weight relative to the total weight of the composition.
13. A composition according to claim 12, wherein said at least one solvent is present in a concentration ranging from 0.5% to 20% by weight relative to the total weight of the composition.
14. A composition according to claim 1, wherein said at least one oxidation dye is chosen from at least one oxidation base and at least one coupler.
15. A composition according to claim 14, wherein said at least one oxidation base is chosen from ortho- and para- phenylenediamines, bisphenylalkylenediamines, ortho- and para-aminophenols, heterocylic bases, and the acid addition salts of all of said at least one oxidation bases.

16. A composition according to claim 14, wherein said at least one oxidation base is present in a concentration ranging from 0.0005% to 12% by weight relative to the total weight of the composition.

17. A composition according to claim 14, wherein said at least one coupler is chosen from meta-phenylenediamines, meta-aminophenols, meta-diphenols, heterocyclic couplers, and the acid addition salts of all of said at least one couplers.

18. A composition according to claim 14, wherein said at least one coupler is present in a concentration ranging from 0.0001% to 10% by weight relative to the total weight of the composition.

19. A composition according to claim 15, wherein said acid addition salts of the oxidation bases are chosen from hydrochlorides, hydrobromides, sulphates, tartrates, lactates and acetates.

20. A composition according to claim 17, wherein said acid addition salts of the couplers are chosen from hydrochlorides, hydrobromides, sulphates, tartrates, lactates and acetates.

21. A composition according to claim 1, further comprising at least one direct dye.

22. A composition according to claim 1, further comprising at least one carrier other than said at least one solvent appropriate for keratinous fibers.

23. A composition according to claim 22, wherein said at least one other carrier comprises water and at least one additional solvent.

24. A composition according to claim 23, wherein said at least one additional solvent is chosen from organic solvents.

25. A composition according to claim 1, wherein the pH varies from about 4 to about 11.

26. A composition according to claim 25, wherein the pH varies from about 6 to about 9.

27. A composition according to claim 1, further comprising at least one suitable cosmetic adjuvant chosen from surfactants, polymers, thickening agents, antioxidants, enzymes different from said at least one enzyme of the laccase type as defined in claim 23, penetrating agents, sequestering agents, perfumes, buffers, dispersing agents, film-forming agents, screening agents, vitamins, preservatives and opacifying agents.

28. A method of dyeing keratinous fibers, comprising applying to said keratinous fibers for a sufficient time to develop a desired color at least one dyeing composition comprising:
  (a) at least one enzyme of the laccase type;
  (b) at least one solvent chosen from
    branched and unbranched $C_3$–$C_8$ $\alpha\omega$-diols;
    branched and $C_5$–$C_8$ 1,2; 1,4; 1,5; 2,3; 2,4; 2,5; 2,6; 2,7; 2,8; 3,4; 3,5; unbranched and 3,6 diols;
    branched and unbranched $C_6$–$C_8$ 1,3 diols;
    $C_4$–$C_8$ triols;
    diethylene glycol and dipropylene glycol;
    $C_3$–$C_8$ monoalkyl ethers of $C_3$–$C_9$ glycols;
    $C_5$–$C_9$ monoalkyl ethers of ethylene glycol;
    $C_1$–$C_2$ monoalkyl ethers of $C_5$–$C_9$ glycols;
    $C_2$ monoalkyl ethers of 1,2; 1,3; 1,4 and 2,3- butanediols;
    monoalkyl ethers of glycols, wherein a total number of carbon atoms is equal to 5;
    $C_1$–$C_9$ dialkyl ethers of $C_2$–$C_9$ glycols; and
    phenyl ethers of $C_3$–$C_9$ glycols; and
  (c) at least one oxidation dye.

29. A method of dyeing keratinous fibers according to claim 28, wherein said keratinous fibers are human keratinous fibers.

30. A method of dyeing keratinous fibers according to claim 29, wherein said human keratinous fibers are hair.

31. A method of dyeing keratinous fibers, comprising the steps of
  (a) storing a first composition,
  (b) storing a second composition separately from said first composition,
  (c) mixing the first composition with the second composition to form a mixture, and
  (d) applying said mixture to said keratinous fibers for a time sufficient to achieve a desired coloration,
  wherein said first composition comprises, in a medium appropriate for dyeing, at least one oxidation dye,
  wherein said second composition comprises, in a medium appropriate for keratinous fibers, said at least one enzyme of the laccase type, and
  further wherein at least one of said first composition and said second composition comprises at least one solvent chosen from
    branched and unbranched $C_3$–$C_8$ $\alpha\omega$-diols;
    branched and $C_5$–$C_8$ 1,2; 1,4; 1,5; 2,3; 2,4; 2,5; 2,6; 2,7; 2,8; 3,4; 3,5; unbranched and 3,6 diols;
    branched and unbranched $C_6$–$C_8$ 1,3 diols;
    $C_4$–$C_8$ triols;
    diethylene glycol and dipropylene glycol;
    $C_3$–$C_8$ monoalkyl ethers of $C_3$–$C_9$ glycols;
    $C_5$–$C_9$ monoalkyl ethers of ethylene glycol;
    $C_1$–$C_2$ monoalkyl ethers of $C_5$–$C_9$ glycols;
    $C_2$ monoalkyl ethers of 1,2; 1,3; 1,4 and 2,3- butanediols;.
    monoalkyl ethers of glycols, wherein a total number of carbon atoms is equal to 5;
    $C_1$–$C_9$ dialkyl ethers of $C_2$–$C_9$ glycols; and
    phenyl ethers of $C_3$–$C_9$ glycols.

32. A multicompartment device or a dyeing kit, comprising a first compartment containing a composition (A) comprising, in a medium appropriate for dyeing, at least one oxidation dye and a second compartment containing a composition (B) comprising, in a medium appropriate for keratinous fibers, at least one enzyme of the laccase type, wherein at least one of said composition (A) and said composition (B) comprises at least one solvent chosen from
    branched and unbranched $C_3$–$C_8$ $\alpha\omega$-diols;
    branched $C_5$–$C_8$ 1,4; 1,4; 1,5; 2,3; 2,4; 2,5; 2,6; 2,7; 2,8; 3,4; 3,5; and unbranched - and 3,6 diols;
    branched and unbranched $C_6$–$C_8$ 1,3 diols;
    $C_4$–$C_8$ triols;
    diethylene glycol and dipropylene glycol;
    $C_3$–$C_8$ monoalkyl ethers of $C_3$–$C_9$ glycols;
    $C_5$–$C_9$ monoalkyl ethers of ethylene glycol;
    $C_1$–$C_2$ monoalkyl ethers of $C_5$–$C_9$ glycols;
    $C_2$ monoalkyl ethers of 1,2; 1,3; 1,4 and 2,3- butanediols;
    monoalkyl ethers of glycols, wherein a total number of carbon atoms is equal to 5;
    $C_1$–$C_9$ dialkyl ethers of $C_2$–$C_9$ glycols; and
    phenyl ethers of $C_3$–$C_9$ glycols.

* * * * *

UNITED STATES PATENT AND TRADEMARK OFFICE
CERTIFICATE OF CORRECTION

PATENT NO. : 6,551,359 B1
DATED : April 22, 2003
INVENTOR(S) : Gérard Lang et al.

It is certified that error appears in the above-identified patent and that said Letters Patent is hereby corrected as shown below:

Title page,
Item [57], ABSTRACT,
Line 7, "method" should read -- methods --.

Column 11,
Line 55, "$C_3$-$C_8\alpha\omega$-*diols*;" should read -- $C_3$-$C_8\alpha\omega$-diols; --.
Line 57, "-and" should read -- and --.

Column 13,
Line 41, "claim 23," should read -- claim 1, --.
Line 52, before "$C_5$-$C_8$", insert -- unbranched --.
Line 53, after "3,5;", delete "unbranched".

Column 14,
Line 27, before "$C_5$-$C_8$", insert -- unbranched --.
Line 28, after "3,5;", delete "unbranched".
Lines 35-36, "butanediols;." should read -- butanediols; --.
Line 50, "branched $C_5$-$C_8$ 1,4;" should read -- branched and unbranched $C_5$-$C_8$ 1,2; --.
Line 51, after "3,5;", delete and "unbranched -"

Signed and Sealed this

Twenty-sixth Day of August, 2003

JAMES E. ROGAN
*Director of the United States Patent and Trademark Office*